(12) United States Patent
Jones et al.

(10) Patent No.: US 7,491,834 B2
(45) Date of Patent: Feb. 17, 2009

(54) CHEMICAL PROCESS

(75) Inventors: Raymond Vincent Heavon Jones, Grangemouth (GB); Alan John Whitton, Grangemouth (GB); Colin John Bennie, Grangemouth (GB); David John Ritchie, Grangemouth (GB); Pascal Bugnon, Monthey (CH)

(73) Assignees: Syngenta Crop Protection, Inc., Greensboro, NC (US); Syngenta Limited (GB)

( * ) Notice: Subject to any disclaimer, the term of this patent is extended or adjusted under 35 U.S.C. 154(b) by 385 days.

(21) Appl. No.: 10/513,564

(22) PCT Filed: Apr. 8, 2003

(86) PCT No.: PCT/GB03/01503

§ 371 (c)(1), (2), (4) Date: May 2, 2005

(87) PCT Pub. No.: WO03/095442

PCT Pub. Date: Nov. 20, 2003

(65) Prior Publication Data

US 2006/0163159 A1 Jul. 27, 2006

(30) Foreign Application Priority Data

May 7, 2002 (GB) .................................. 0210370.3

(51) Int. Cl.
*C07D 311/00* (2006.01)

(52) U.S. Cl. ..................................................... 549/290
(58) Field of Classification Search .................. 549/290
See application file for complete search history.

(56) References Cited

U.S. PATENT DOCUMENTS 6,008,381 A * 12/1999 Williams et al. ............ 549/290
6,372,921 B1 * 4/2002 Miyota et al. ............... 549/290

FOREIGN PATENT DOCUMENTS

| EP | 1054009 | 11/2000 |
| EP | 1072580 | 1/2001 |
| WO | 9748692 | 12/1997 |

* cited by examiner

*Primary Examiner*—D. Margaret Seaman
*Assistant Examiner*—Nizal S Chandrakumar
(74) *Attorney, Agent, or Firm*—James Cueva

(57) ABSTRACT

3-Isochromanone is prepared by partially chlorinating o-tolylacetic acid with sulphuryl chloride or chlorine gas in an inert organic solvent in the presence of a free radical initiator. The 2-chloromethylphenylacetic acid first obtained is converted to 3-isochromanone by treatment with a base and separated from unreacted o-tolylacetic acid, which is in the form of a salt, by a phase separation technique. The separated o-tolylacetic acid salt is converted to o-tolylacetic acid by controlled acidification and the o-tolylacetic acid is extracted for re-use. The invention reduces the formation of unwanted, over-chlorinated by-products and leads to a more efficient process.

13 Claims, No Drawings

CHEMICAL PROCESS

This application is a 371 of International Application No. PCT/GB03/01503 filed Apr. 8, 2003, which claims priority to GB 0210370.3, filed May 7, 2002, the contents of which are incorporated herein by reference.

This invention relates to a chemical process and more particularly to a process for preparing 3-isochromanone, which is useful in the manufacture of certain agrochemicals.

3-Isochromanone is a well-known compound having the formula:

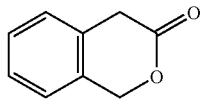

Several methods for its preparation are described in the chemical literature. One such method, described in WO 97/48692, involves the radical chlorination of o-tolylacetic acid with sulphuryl chloride to form 2-chloromethylphenylacetic acid, which is then ring-closed using a base to form 3-isochromanone. A similar method is described in EP-A-1072580 where chlorine gas is used instead of sulphuryl chloride.

In WO 97/48692 it is stated that any amount of sulphuryl chloride may be used but, for efficiency, it is desirable to use at least one mole of sulphuryl chloride per mole of o-tolylacetic acid and preferably a molar excess up to 1.5 moles per mole. In EP-A-1072580 it is stated that the amount of chlorine gas used is preferably from 0.2 to 2 mol, and more preferably from 0.8 to 1.2 mol, based on one mol of the o-tolylacetic acid. However, in all the examples 19 g of chlorine is used for 30 g of o-tolylacetic acid, which is about 1.33 moles per mole. No benefit is claimed or demonstrated for the use of a lower ratio of chlorine.

An issue with these prior art processes from a commercial viewpoint is that unwanted, over-chlorinated by-products are formed (such as 2-dichloromethylphenylacetic acid and 2-chloromethyl-α-chlorophenylacetic acid), thereby reducing the efficiency of the conversion of the o-tolylacetic acid starting material to 3-isochromanone. The present invention provides an improved process which alleviates this problem.

Thus according to the present invention there is provided a process for the preparation of 3-isochromanone which comprises the steps of:

(a) partially chlorinating o-tolylacetic acid with sulphuryl chloride or chlorine gas in an inert organic solvent in the presence of a free radical initiator to form a reaction mixture containing 2-chloromethylphenylacetic acid and unreacted o-tolylacetic acid;

(b) treating the reaction mixture from step (a) with an aqueous salt-forming base to convert the 2-chloromethylphenylacetic acid to 3-isochromanone and to form a salt of the unreacted o-tolylacetic acid, preferably in the presence of a catalytic amount of potassium iodide;

(c) separating the 3-isochromanone from the salt of o-tolylacetic acid obtained in step (b) by a phase separation technique, the 3-isochromanone being dissolved in a water-immiscible organic solvent and the o-tolylacetic acid salt being dissolved in an aqueous solution; and (d) converting the separated o-tolylacetic acid salt to o-tolylacetic acid by controlled acidification of the aqueous solution separated in step (c), extracting the o-tolylacetic acid so formed into a solvent suitable for use in step (a) and recycling the solvent extract in a subsequent operation of step (a).

The inert organic solvent employed in step (a) and step (d) of the process is inert to the reactants and is of a type suitable for use with free radical chlorination reactions. Depending on how step (b) of the process is carried out (as discussed later), it is preferred to use a water-immiscible inert organic solvent. Such solvents include, for example, aromatic hydrocarbons such as benzene or halogenated or polyhalogenated aromatic hydrocarbons such as monochlorobenzene, dichlorobenzenes, for example, o-dichlorobenzene, trichlorobenzenes, monofluorobenzene, trifluoromethylbenzene, bistrifluoromethylbenzenes and chlorotrifluoromethylbenzenes.

The partial chlorination reaction is usually carried out at an elevated temperature, normally in the range of from 20° C. to 95° C. When the chlorinating agent is sulphuryl chloride the temperature is suitably from 50° C. to 90° C., for example, from 60° C. to 85° C., and typically from 75° C. to 80° C. When the chlorinating agent is chlorine gas the temperature is suitably from 40° C. to 85° C., for example, from 60° C. to 85° C., and typically from 75° C. to 80° C.

By partial chlorination is meant the deliberate under-reaction of the chlorinating agent with the o-tolylacetic acid. The object is to ensure that the major product of the reaction is 2-chloromethylphenylacetic acid with a minimum of over-chlorinated by-products and to recycle unreacted o-tolylacetic acid. This may be achieved by using from 0.2 to 1.2 moles of chlorinating agent for each mole of o-tolylacetic acid, for example, from 0.4 to 1.2 moles per mole, suitably from 0.7 to 1.1 moles per mole, and typically from 0.75 to 0.99 moles per mole of o-tolylacetic acid.

The free radical initiator may be a suitable source of heat or light, for example ultra-violet light, or a chemical compound of a type typically used to initiate free radical reactions, such as a peroxide, a peracid or an azo compound. Particularly suitable are 2,2'-azobis (2-methylbutyronitrile) and 2,2'-azobisisobutyronitrile. The quantity of chemical initiator used is typically from 0.005 to 0.1 moles per mole of o-tolylacetic acid, for example from 0.01 to 0.05 moles per mole.

The salt-forming base used in step (b) is suitably an alkali or alkaline earth metal hydroxide, phosphate, carbonate, or bicarbonate, for example, sodium hydroxide, potassium hydroxide, sodium phosphate, sodium carbonate, potassium carbonate, sodium bicarbonate or potassium bicarbonate. The presence of potassium iodide has been found to enhance the ring closure processes and improve yields.

Step (b) of the process may be carried out in either of two ways. Either:

(1) the reaction mixture from step (a) is treated with an aqueous salt-forming base to form directly 3-isochromanone and an o-tolylacetic acid salt at a controlled pH; or (2) the 2-chloromethylphenylacetic acid and o-tolylacetic acid are extracted from the reaction mixture from step (a) at high pH (viz. at a pH above 10, typically above 12) with a strong aqueous base to give an aqueous solution of an o-tolylacetic acid salt and a 2-hydroxymethylphenylacetic acid salt, the aqueous extract suitably acidified to convert the 2-hydroxymethylphenylacetic acid to 3-isochromanone and the o-tolylacetic acid salt to o-tolylacetic acid, and, in the presence of an added water-immiscible organic solvent, the pH adjusted with a salt-forming base to reconvert the o-tolylacetic acid to an o-tolylacetic acid salt.

In (1), it is important that the inert organic solvent used in step (a) is a water-immiscible immiscible solvent. This is so that the 3-isochromanone, which is dissolved in the solvent, may be directly separated from the o-tolylacetic acid salt, which is dissolved in the aqueous phase, in step (c) of the process. In this case the pH is suitably adjusted in a range of from 4 to 8, more suitably, in a range of from 6 to 8, for example, in a range of from 6 to 7, and typically in a range of from 6.3 to 6.8. At this pH 2-chloromethylphenylacetic acid is converted to 3-isochromanone and a salt of o-tolylacetic acid is formed. The pH adjustment is conveniently carried out using the salt-forming base, which will normally be an alkali metal or alkaline earth metal base. This may be a strong base, normally a hydroxide, or a mild base, such as a bicarbonate, or a combination of the two. Thus, for example, the pH may be adjusted with an initial charge of sodium or, preferably, potassium hydroxide, followed by a finer adjustment with sodium or, preferably, potassium bicarbonate. Catalytic amounts of potassium iodide have been found to enhance the ring closure process.

In (2), a strong aqueous alkali metal or alkaline earth metal base, typically sodium or potassium hydroxide, is used initially to ring close the 2-chloromethylphenylacetic acid to form 3-isochromanone which, at high pH, ring opens to form a water soluble 2-hydroxy-methylphenylacetic acid salt, and to extract the 2-hydroxymethylphenylacetic acid and the o-tolylacetic acid salts from the organic reaction mixture obtained in step (a) of the process. The aqueous extract may then be mixed with the same or a different water-immiscible organic solvent and acidified to a pH below 4, suitably to a pH of 1, using, for example, a strong mineral acid such as hydrochloric acid. This converts (ring-closes) the 2-hydroxymethylphenylacetic acid to 3-isochromanone and reforms the o-tolylacetic acid from its salt. Controlled basification using a salt-forming base to a pH of from 4 to 8, more suitably, from 6 to 8, as described for (1) above, converts the o-tolylacetic acid to a salt, which dissolves in the aqueous phase, while the 3-isochromanone remains in solution in the solvent. The organic and aqueous phases may then be separated in step (c) using conventional liquid phase separation techniques.

In step (d) of the process, the o-tolylacetic acid salt is conveniently extracted from the aqueous phase by controlled acidification in the presence of a water-immiscible solvent suitable for use in step (a) of the process. Controlled acidification to a pH of 4 or below, suitably to a pH in the range of from 2 to 4 and especially to a pH in the range of from 3 to 3.6, converts the o-tolylacetic acid salt to o-tolylacetic acid, which dissolves in the solvent. Unwanted acidic species are retained in the aqueous layer. The solvent, containing dissolved o-tolylacetic acid, may then be separated from the aqueous phase by conventional liquid phase separation techniques and recycled directly in a subsequent step (a).

Thus, in a typical process, the o-tolylacetic acid is partially chlorinated with sulphuryl chloride or chlorine gas using the general procedures described in WO 97/48692 and EP-A-1072580. When chlorination has proceeded as far as desired, for example, when over half of the o-tolylacetic acid has been converted to 2-chloromethylphenylacetic acid, the reaction mixture is held at about 60° C. and water and base added to adjust the pH to, for example, 6 to 8, preferably pH 6 to 7. This results in the ring closure of the 2-chloromethylphenylacetic acid to 3-isochromanone and deprotonates the residual o-tolylacetic acid, extracting it into the aqueous layer. Other acid by-products are also extracted with it.

The aqueous layer, when acidified in the presence of a substantially water-immiscible solvent (e.g. fluorobenzene or chlorobenzene) reforms the o-tolylacetic acid, which dissolves in the solvent. The solvent may then be separated from the aqueous layer and directly recycled in the chlorination process. Although a number of complete recycles are possible, a purge of the recycled stream can be included if impurities build up. This technique may be used to enhance the yield of 3-isochromanone from o-tolylacetic acid by increasing the efficiency of the o-tolylacetic acid conversion to 3-isochromanone.

The organic layer containing the 3-isochromanone may be treated in one of two ways. Either the solvent may be separated from the 3-isochromanone, for example by distillation under reduced pressure, and recovered or recycled. This leaves a melt of 3-isochromanone which can be purified further, if necessary, by standard techniques, for example, by distillation or by crystallisation (either melt or solvent crystallisation). Or the solvent may be treated with an aqueous base, such as potassium hydroxide, to extract the 3-isochromanone as an aqueous solution of ring opened 3-isochromanone (2-hydroxymethylphenylacetic acid). Separation of the 3-isochromanone from the organic layer may be enhanced by multiple extractions or by counter-current extraction techniques. Acidification of this aqueous extract to pH 1 (giving ring closure to 3-isochromanone) in the presence of an organic solvent, such as benzene, fluorobenzene, chlorobenzene, xylene, toluene,-methyl-tert-butyl ether, cyclohexanone or dichloromethane, leaves an organic solution of 3-isochromanone which may be isolated by, for example, solvent evaporation or other conventional techniques.

Alternatively, the o-tolylacetic acid, 3-isochromanone and other acidic by-products may be extracted from the reaction mixture obtained in step (a) with, for example, aqueous potassium hydroxide. The aqueous layer may then be mixed with a solvent (e.g. toluene, oxylene, fluorobenzene, etc.) and acidified to pH 1 at, for example, 60° C. to reconvert the aqueous salts to the 3-isochromanone and o-tolylacetic acid. Separation of the o-tolylacetic acid and most other acid species from the 3-isochromanone is achieved by adjustment of the solution of o-tolylacetic acid and 3-isochromanone to a pH of from 4 to 8, for example from 6 to 8 and preferably from 6 to 7 by the use of a salt-forming base, such as an alkali or alkaline earth metal hydroxide, phosphate, carbonate, or bicarbonate, for example, sodium hydroxide, potassium hydroxide, sodium phosphate, sodium carbonate, potassium carbonate, sodium bicarbonate or, typically, potassium bicarbonate. The resultant aqueous layer may then be recycled and the 3-isochromanone, dissolved in the solvent, may either be used as made or purified by standard techniques.

The invention is illustrated by the following Examples.

EXAMPLE 1

0-Tolylacetic acid (346.5 g, 2.307 moles) was charged to a glass reactor fitted with stirrer, thermometer condenser and vented to a caustic scrubber. Fluorobenzene (476.2 g, 4.96 moles) was added and the contents heated to 75-80° C. with stirring. To the mixture was added 2,2'-azobis (2-methylbutyronitrile) (8.9 g, 0.046 moles) in fluorobenzene (79.7 g, 0.83 moles). Sulphuryl chloride (311.4 g, 2.307 moles) was added over 3 hours while maintaining the temperature at 75-80° C. After the addition was complete, the mixture was held for 1 hour at 75-80° C. The temperature was adjusted to 60° C. and 50% potassium hydroxide (180.9 g, 1.615 moles) added, followed by potassium iodide (1.53 g, 0.009 moles). The pH was then adjusted to 6.3 using 20% potassium bicarbonate. After settling, the aqueous phase was separated from the organic phase.

The aqueous phase was held for extraction and re-cycle of the o-tolylacetic acid.

The organic phase was distilled to remove the fluorobenzene and leave the crude 3-isochromanone 286.6 g at 81% strength w/w (equivalent to 232 g @100% wt, 1.568 moles) representing a yield of 68% from o-tolylacetic acid.

The aqueous phase (1042 g) was charged to a reaction vessel containing fluorobenzene (524 g, 5.458 moles) and 36% hydrochloric acid (55 g, 0.542 moles) was added to reduce the pH to 1.0. The organic and aqueous phases were stirred, allowed to settle and separated. Analysis of the upper fluorobenzene layer (642.2 g) showed it contained 3.1% o-tolylacetic acid (19.9 g, 0.13 moles) equivalent to 6% of the original charge. This layer was recycled for use in a subsequent preparation.

EXAMPLE 2 o-Tolylacetic acid (3.96 kg, 26.36 moles) was charged to a 20 liter glass reactor fitted with stirrer, thermometer and condenser and vented to a caustic scrubber. Chlorobenzene (6 kg, 53.3 moles) was added and the contents heated to 78-79° C. with stirring. To the mixture was added 2,2'-azobis (2-methylbutyronitrile) (0.103 kg, 0.54 moles) in chlorobenzene (0.93 kg, 8.3 moles). Sulphuryl chloride (2.86 kg, 21.34 moles) was added over 3 hours while maintaining the temperature at 75-80° C. After the addition was complete, the mixture was held for 1 hour at 78-80° C. The temperature was adjusted to 60° C. and 50% potassium hydroxide (1.4 kg, 12.5 moles) was added, followed by 30% potassium iodide (0.05 kg, 0.09 moles). The pH was then adjusted to 6.8 using 20% potassium bicarbonate (11.2 kg, 22.4 moles). After settling, the aqueous layer was separated from the organic phase. The organic phase was given a further aqueous potassium bicarbonate wash at pH 6.8 (4.8 kg containing 0.06 kg, 0.6 moles potassium bicarbonate). The two aqueous washes were combined for recycling.

The organic phase was distilled to remove some of the chlorobenzene and water. Methylcyclohexane was added (6 kg, 61.2 moles). The solution of 3-isochromanone was cooled to −5° C. and the 3-isochromanone isolated by filtration followed by washing with methylcyclohexane. The isolated 3-isochromanone weighed 1.8 kg (12.2 moles), at 98% strength w/w and contained less than 1% o-tolylacetic acid. The isolated yield was 45% from the o-tolylacetic acid charged (60% from the o-tolylacetic acid consumed taking into account the o-tolylacetic acid recovered).

The combined aqueous washes saved for recycling (ca. 15.9 kg) were charged to a reaction vessel containing chlorobenzene (4 kg, 35.6 moles). Hydrochloric acid 32% strength (1.1 kg, 9.6 moles) was added to reduce the pH to 3.5. The phases were then settled and separated. Analysis of the upper chlorobenzene layer showed it contained o-tolylacetic acid (0.96 kg, 6.4 moles) equivalent to 24.2% of the original charge. This layer was re-cycled in a subsequent preparation as part of the batch charge.

EXAMPLE 3 o-Tolylacetic acid (3.04 kg, 20.3 moles) was charged to a 20 liter glass reactor fitted with stirrer, thermometer and condenser and vented to a caustic scrubber. Chlorobenzene containing re-cycled o-tolylacetic acid (5.23 kg at 18.3% equivalent to 0.96 kg 100%, 6.4 moles) recovered from Example 2 was added followed by a make up charge of chlorobenzene (1.5 kg/13.3 moles) to give a total chlorobenzene charge of 6 kg (53.3 moles). The contents were heated to 78-79° C. with stirring. To the mixture was added 2,2'-azobis (2-methylbutyronitrile) (0.103 kg, 0.54 moles) in chlorobenzene (0.93 kg, 8.3 moles). Sulphuryl chloride (3.28 kg, 24.2 moles) was added over 3 hours maintaining the temperature at 75-80° C. After the addition was complete, the mixture was held for 1 hour at 78-80° C. The temperature was adjusted to 60° C. and 2 kg of water were added followed by 50% potassium hydroxide (2 kg, 17.8 moles). Potassium iodide 30% (0.05 kg, 0.09 moles) was added and the pH was then adjusted to 6.8 using 20% potassium bicarbonate (10.7 kg, 21.5 moles). After settling, the aqueous phase was separated from the organic phase for extraction and recycling of the o-tolylacetic acid.

The organic phase was distilled to remove some of the chlorobenzene and water. Methylcyclohexane was added (6 kg, 61.2 moles). The solution of 3-isochromanone was cooled to −5° C., the 3-isochromanone isolated by filtration and washed with methylcyclohexane. The isolated 3-isochromanone weighed 1.65 kg (98% strength w/w, 11.15 moles). The isolated yield was 41% from o-tolylacetic acid charged (58% from o-tolylacetic acid consumed taking into account the o-tolylacetic acid recovered).

The aqueous phase saved for recycling (ca. 17.1 kg) was charged to a reaction vessel containing chlorobenzene (4 kg, 35.6 moles). Hydrochloric acid 32% strength (1.36 kg, 11.9 moles) was added to reduce the pH to 3.5. The phases were then settled and separated. Analysis of the upper chlorobenzene layer showed it to contain o-tolylacetic acid (1.19 kg, 7.9 moles) equivalent to 29.6% of the original charge.

This layer was held for re-cycling in a subsequent preparation as part of the batch charge.

EXAMPLE 4 o-Tolylacetic acid (3.96 kg, 26.4 moles) was charged to a 20 liter glass reactor fitted with stirrer, thermometer, condenser and scrubber. Chlorobenzene (6 kg) was charged to the reaction vessel and the contents heated to 78-79° C. A solution of 2,2'-azobis (2-methylbutyronitrile) (103 g) in chlorobenzene (930 g) was added to the vessel. This was followed by sulphuryl chloride (2.86 kg, 22.19 moles) added at a steady rate over 3 hours. After complete addition, the reaction mixture was held for an hour. Potassium hydroxide (50% w/w solution, 1.4 kg) was dosed to the reactor to control an exotherm. Potassium iodide (30% aqueous solution, 50 g) was then added. The pH was finally adjusted to 6.8 with 20% potassium bicarbonate solution (11.2 kg). The aqueous layer was separated from the organic layer and recycled. The organic layer was washed with water (4.5 kg) and the pH adjusted to 6.8 with 20% potassium bicarbonate solution (0.3 kg). The aqueous layer was separated from the organic layer and recycled with the first aqueous phase. The organic layer was distilled to remove water, and some chlorobenzene for recycle. Methylcyclohexane (6 kg) was then added to provide a ratio of methylcyclohexane:chlorobenzene of 50:50% w/w. The solution was cooled from 65° C. down to −5° C., and purified 3-isochromanone crystallised. The 3-isochromanone formed, 1.79 kg (98% strength w/w, 11.9 mol). The isolated yield was 1.79 kg at 98% strength w/w, 11.9 mol or 45% of theory (59% of OTAA consumed taking into account the o-tolylacetic acid recovered). Both aqueous layers (15.9 kg) were charged to a reaction vessel and chlorobenzene (4 kg) added. The pH was adjusted with concentrated hydrochloric acid solution (32% w/w, 1.1 kg) to 3.5 and the aqueous layer separated. A sample of the organic layer was sampled and analysed for o-tolylacetic acid. This indicated that about 0.96 kg of o-tolylacetic acid was present (24% of the original charge). Also present was about 220 g of 3-isochromanone (5% of the original charge).

EXAMPLE 5 o-Tolylacetic acid (3.96 kg, 26.36 moles) was charged to a 20 liter glass reactor fitted with stirrer, thermometer and condenser and vented to a caustic scrubber. Chlorobenzene (6 kg, 53.3 moles) was added. The contents were heated to 78-79° C. with stirring. To the mixture was added 2,2'-azobis (2-methylbutyronitrile) (0.103 kg, 0.54 moles) in chlorobenzene is (0.93 kg, 8.3 moles). Sulphuryl chloride (2.93 kg, 21.67 moles) was added over 3 hours maintaining the temperature at 75-80° C. After the addition was complete, the mixture was held for 1 hour at 78-80° C. The temperature was adjusted to 60° C. and water (0.95 kg) was added followed by 50% potassium hydroxide (1.4 kg, 24.96 moles). Potassium iodide 30% (0.05 kg, 0.09 moles) was added and the pH was then adjusted to 6.8 using 20% potassium bicarbonate (11.21 kg, 22.39 moles). After settling, the aqueous layer was separated from the organic phase for extraction and recycling of the o-tolylacetic acid.

The organic phase was distilled to remove some of the chlorobenzene and water. Methylcyclohexane was added (6 kg, 61.2 moles), the chlorobenzene and methylcyclohexane ratio being 50/50% w/w. The solution was cooled to −5° C., the 3-isochromanone isolated by filtration and washed with methylcyclohexane. The isolated 3-isochromanone (1.78 kg at 98.1% strength w/w, 11.8 mol) contained less than 0.1% o-tolylacetic acid. The isolated yield was 44.7% from the o-tolylacetic acid charged, or 58.7% from the o-tolylacetic acid consumed taking into account the o-tolylacetic acid recovered.

The aqueous phase (ca 15.1 kg) was charged to a reaction vessel containing chlorobenzene (4 kg, 35.52 moles). Hydrochloric acid 32% strength (1.12 kg, 9.8 moles) was added to adjust the pH to 3.5. The phases were then settled and separated. The upper chlorobenzene layer contained o-tolylacetic acid (0.94 kg, 6.3 moles, 23.9% of the original charge), and 3-isochromanone (0.18 kg, 1.2 moles). This layer was held for re-cycling in Example 6 as part of the batch charge.

EXAMPLE 6 o-Tolylacetic acid (3.04 kg, 20.27 moles) was charged to a 20 liter glass reactor fitted with stirrer, thermometer and condenser and vented to a caustic scrubber. Chlorobenzene containing the re-cycled o-tolylacetic acid from Example 5 (5.23 kg at 17.8% o-tolylacetic acid; 0.93 kg at 100%, 6.2 moles) was added followed by a make up charge of chlorobenzene (2.0 kg, 17.8 moles). The contents were heated to 78-79° C. with stirring. To the mixture was added 2,2'-azobis (2-methylbutyronitrile) (0.103 kg, 0.54 moles) in chlorobenzene (0.93 kg, 8.3 moles). Sulphuryl chloride (3.28 kg, 24.3 moles) was added over 3.5 hours maintaining the temperature at 75-80° C. After the addition was complete, the mixture was held for 1 hour at 78-80° C. The temperature was adjusted to 60° C. and 2 kg of water was added followed by 50% potassium hydroxide (2 kg, 17.8 moles) Potassium iodide 30% (0.05 kg, 0.09 moles) was added and the pH was adjusted to 6.8 using 20% potassium bicarbonate (10.8 kg, 21.6 moles). After settling, the aqueous phase was separated from the organic phase for extraction and re-cycling of the o-tolylacetic acid.

The organic phase was distilled to remove some of the chlorobenzene/water. Methylcyclohexane was added (6 kg, 61.2 moles), the chlorobenzene/methylcyclohexane ratio being 50/50% w/w. The solution was cooled to −5° C., the 3-isochromanone isolated by filtration and washed with methylcyclohexane. The isolated 3-isochromanone (1.64 kg at 98.9% strength w/w, 11.0 mol) contained less than 0.1% o-tolylacetic acid. The isolated yield was 41.4% from the o-tolylacetic acid charged, or 57.7% from the o-tolylacetic acid consumed taking into account the o-tolylacetic acid recovered.

The aqueous phase (ca. 17.1 kg) was charged to a reaction vessel containing chlorobenzene (4 kg, 35.6 moles). Hydrochloric acid 32% strength (1.36 kg, 11.9 moles) was added to reduce the pH to 3.5. The phases were then settled and separated. The organic phase contained o-tolylacetic acid (1.13 kg, 7.5 moles). This layer was held for re-cycling in Example 7 as part of the batch charge.

EXAMPLE 7 o-Tolylacetic acid (2.81 kg, 18.7 moles) was charged to a 20 liter glass reactor fitted with stirrer, thermometer and condenser and vented to a caustic scrubber. Chlorobenzene containing the re-cycled o-tolylacetic acid (5.31 kg at 21.2% o-tolylacetic acid, 1.12 kg, 7.5 moles) was added followed by a make up charge of chlorobenzene (1.89 kg, 16.8 moles) to give a total chlorobenzene charge of 6.1 kg (53.9 moles). The contents were heated to 78-79° C. with stirring. To the mixture was added 2,2'-azobis (2-methylbutyronitrile) (0.103 kg, 0.54 moles) in chlorobenzene (0.93 kg, 8.3 moles). Sulphuryl chloride (3.86 kg, 28.6 moles) was added over 4 hours maintaining the temperature at 75-80° C. After the addition was complete, the mixture was held for 1 hour at 78-80° C. The temperature was adjusted to 60° C. and 50% potassium hydroxide added (2 kg, 17.8 moles). Potassium iodide 30% (0.05 kg, 0.09 moles) was added and the pH was adjusted to 6.8 using 20% potassium bicarbonate (10.62 kg, 21.2 moles). After settling, the aqueous phase was separated from the organic phase for extraction and re-cycling of the o-tolylacetic acid.

The organic phase was distilled to remove some of the chlorobenzene/water. Methylcyclohexane was added (5.5 kg, 56 moles), the chlorobenzene/methylcyclohexane ratio being 43/57% w/w. The solution was cooled to −5° C., the 3-isochromanone isolated by filtration and washed with methylcyclohexane. The isolated 3-isochromanone (2.12 kg at 96.4% strength w/w, 13.8 mol) contained 0.1% o-tolylacetic acid. The isolated yield was 52.6% from the o-tolylacetic acid charged, or 66.0% from the o-tolylacetic acid consumed taking into account the o-tolylacetic acid recovered.

The aqueous phase (ca. 16.95 kg) was charged to a reaction vessel containing chlorobenzene (4 kg, 35.6 moles). Hydrochloric acid 32% strength (1.07 kg, 9.4 moles) was added to adjust the pH to 3.5. The phases were then settled and separated. The organic layer contained o-tolylacetic acid (0.79 kg, 5.3 moles). This layer was held for re-cycling in Example 8 as part of the batch charge.

EXAMPLE 8 o-Tolylacetic acid (3.71 kg, 24.7 moles) was charged to a 20 liter glass reactor fitted with stirrer, thermometer and condenser and vented to a caustic scrubber. Chlorobenzene containing the re-cycled o-tolylacetic acid from Example 7 (4.98 kg at 15.9% o-tolylacetic acid, 0.79 kg, 5.3 moles) was added followed by a make up charge of chlorobenzene (1.8 kg, 16 moles) to give a total chlorobenzene charge of 6.0 kg (53.2 moles). The contents were heated to 78-79° C. with stirring.

To the mixture was added 2,2'-azobis (2-methylbutyronitrile) (0.103 kg, 0.54 moles) in chlorobenzene (0.93 kg, 8.3 moles). Sulphuryl chloride (4.28 kg, 31.7 moles) was added over 4 hours maintaining the temperature at 75-80° C. After the addition was complete, the mixture was held for 1 hour at 78-80° C. The temperature was adjusted to 60° C. and 50% potassium hydroxide added (2 kg, 17.8 moles). Potassium iodide 30% (0.05 kg, 0.09 moles) was added and the pH was adjusted to 6.8 using 20% potassiunt bicarbonate (12.52 kg, 25.0 moles). After settling, the aqueous phase was separated from the organic phase for extraction and re-cycling of the o-tolylacetic acid.

The organic phase was distilled to remove some of the chlorobenzene/water. Methylcyclohexane was added (6.0 kg, 61.1 moles), the chlorobenzene/methylcyclohexane ratio being 51/49% w/w. The solution was cooled to −5° C., the 3-isochromanone isolated by filtration and washed with methylcyclohexane. The isolated 3-isochromanone (2.30 kg at 96.7% strength w/w, 15.0) contained 0.1% o-tolylacetic acid. The isolated yield was 50.0% from the o-tolylacetic acid charged, or 60.1% from the o-tolylacetic acid consumed taking into account the o-tolylacetic acid recovered.

The aqueous phase (ca 17.96 kg) was charged to a reaction vessel containing chlorobenzene (5 kg, 44.4 moles). Hydrochloric acid 32% strength (1.11 kg, 9.75 moles) was added to reduce the pH to 3.5. The phases were settled and separated. The organic layer contained o-tolylacetic acid (0.76 kg, 5.0 moles).

This layer was held for re-cycling in Example 9 as part of the batch charge.

EXAMPLE 9 o-Tolylacetic acid (4.25 kg, 28.3 moles) was charged to a 20 liter glass reactor fitted with stirrer, thermometer and condenser and vented to a caustic scrubber. Chlorobenzene containing the re-cycled o-tolylacetic acid from Example 8 (5.15 kg at 14.7% o-tolylacetic acid, 0.76 kg, 5.0 moles) was added followed by a make up charge of chlorobenzene (1.1 kg, 9.8 moles) to give a total charge of chlorobenzene of 5.5 kg (48.8 moles). The contents were heated to 78-79° C. with stirring. To the mixture was added 2,2'-azobis (2-methylbutyronitrile) (0.103 kg, 0.54 moles) in chlorobenzene (0.93 kg, 8.3 moles). Sulphuryl chloride (5.05 kg, 37.4 moles) was added over 4 hours maintaining the temperature at 75-80° C. After the addition was complete, the mixture was held for 1 hour at 78-80° C. The temperature was adjusted to 60° C. and 50% potassium hydroxide added (2.5 kg, 22.3 moles). Potassium iodide 30% (0.05 kg, 0.09 moles) was added and the pH was adjusted to 6.8 using 20% potassium bicarbonate (12.18 kg, 24.3 moles). After settling the aqueous phase was separated from the organic phase for extraction and re-cycling of the o-tolylacetic acid.

The organic phase was distilled to remove some of the chlorobenzene/water. Methylcyclohexane was added (6.0 kg, 61.1 moles), the chlorobenzene/methylcyclohexane ratio being 56/44% w/w. The solution was cooled to −5° C., the 3-isochromanone isolated by filtration and washed with methylcyclohexane. The isolated 3-isochromanone (3.03 kg at 93.2% strength w/w) contained 0.2% o-tolylacetic acid. The isolated yield was 57.3% from the o-tolylacetic acid charged, or 66.3% from the o-tolylacetic acid consumed taking account of the o-tolylacetic acid recovered.

The aqueous phase (ca. 16.55 kg) was charged to a reaction vessel containing chlorobenzene (5 kg, 44.4 moles). Hydrochloric acid 32% strength (1.01 kg, 8.9 moles) was added to reduce the pH to 3.5. The phases were then settled and separated. The organic layer contained o-tolylacetic acid (0.67 kg, 4.5 moles).

EXAMPLE 10 o-Tolylacetic acid (199.5 g, 1.33 moles) was charged to a 1 liter glass reactor fitted with stirrer, thermometer and condenser and vented to a caustic scrubber. Chlorobenzene was added (275 g, 2.44 moles). The contents were heated to 78-79° C. with stirring. To the mixture was added 2,2'-azobis (2-methylbutyronitrile) (5.15 g, 0.027 moles) in chlorobenzene (46.5 g, 0.41 moles). Chlorine (75.5 g, 1.06 moles) was added over 3 hours while maintaining the temperature at 75-80° C. After the addition was complete, the mixture was held for 1 hour at 78-80° C. The temperature was adjusted to 60° C. and water (67 g) was added followed by 50% potassium hydroxide (77.2 g, 0.69 moles) Potassium iodide 30% (2.5 g, 0.0045 moles) was added and the pH was adjusted to 6.4 using 20% potassium bicarbonate (448.8 g, 0.897 moles). After settling, the aqueous phase was separated from the organic phase for extraction and re-cycling of the o-tolylacetic acid.

The organic phase was distilled to remove some of the chlorobenzene/water. Methylcyclohexane was added (300 g, 3.06 moles), the chlorobenzene/methylcyclohexane ratio being 50/50% w/w. The solution was cooled to −5° C. and the 3-isochromanone isolated by filtration followed by methylcyclohexane washing. The isolated 3-isochromanone (85 g at 99.0% strength w/w, 0.57 mol) contained less than 0.1% o-tolylacetic acid. The isolated yield was 42.7% from the o-tolylacetic acid charged, or 58.3% from the o-tolylacetic acid consumed taking into account the o-tolylacetic acid recovered, (63.8% including recovered 3-isochromanone).

The aqueous phase (ca. 686 g) was charged to a reaction vessel containing chlorobenzene (275 g, 2.44 moles). Hydrochloric acid 32% strength (59.5 g, 0.52 moles) was added to reduce the pH to 3.5. The phases were then settled and separated. The organic layer contained o-tolylacetic acid (55.3 g, 0.37 moles), and 3-isochromanone (10.8 g, 0.07 moles). This layer was held for re-cycling in Example 11 as part of the batch charge.

EXAMPLE 11 o-Tolylacetic acid (145.2, 0.967 moles) was charged to a 20 liter glass reactor fitted with stirrer, thermometer and condenser and vented to a caustic scrubber. Chlorobenzene containing the re-cycled o-tolylacetic acid from Example 10 (345 g at 15.8% o-tolylacetic acid; 54.5 g, 0.37 moles) was added. The contents were heated to 78-79° C. with stirring. To the mixture was added 2,2'-azobis (2-methylbutyronitrile) (5.15 g, 0.027 moles) in chlorobenzene (46.5 g, 0.41 moles). Chlorine (75.5 g, 1.063 moles) was added over 3 hours while maintaining the temperature at 75-80° C. After the addition was complete, the mixture was held for 1 hour at 78-80° C. The temperature was adjusted to 60° C. and water (67 g) was added followed by 50% potassium hydroxide (100 g, 0.89 moles). Potassium iodide 30% (2.5 g, 0.0045 moles) was added and the pH was adjusted to 6.4 using 20% potassium bicarbonate (442 g, 0.88 moles). After settling, the aqueous phase was separated from the organic phase for extraction and re-cycling of the o-tolylacetic acid.

The organic phase was distilled to remove some of the chlorobenzene/water. Methylcyclohexane was added (250 g, 2.55 moles), the chlorobenzene/methylcyclohexane ratio being 51/49% w/w. The solution was cooled to −5° C., the 3-isochromanone isolated by filtration and washed with methylcyclohexane. The isolated 3-isochromanone (61.0 g at 98.3% strength w/w) contained less than 0.1% o-tolylacetic acid. The isolated yield was 41.8% from the o-tolylacetic acid charged, or 69.9% from the o-tolylacetic acid consumed taking into account the o-tolylacetic acid recovered.

The aqueous phase (ca. 739 g) was charged to a reaction vessel containing chlorobenzene (275 g, 2.44 moles). Hydrochloric acid 32% strength (84.2 g, 0.74 moles) was added to reduce the pH to 3.5. The phases were settled and separated. The organic layer contained o-tolylacetic acid (55.3 g, 0.373 moles) equivalent to 28.1% of the original charge.

EXAMPLE 12

This Example illustrates a distillative work-up of 3-isochromanone

Chlorobenzene (481 g, 4.27 moles) and o-Tolylacetic acid (350 g, 2.33 moles) were charged to a glass reactor fitted with stirrer, thermometer condenser and vented to a caustic scrubber. Additional chlorobenzene (102.4 g, 0.91 moles) was added and the contents azeotropically dried under vacuum at 75-80° C. with stirring (100.4 g removed). To the mixture was added 2,2'-azobis (2-methylbutyronitrile) (8.95 g, 0.046 moles) in chlorobenzene (80 g, 0.71 moles). Sulphuryl chloride (389.2 g, 2.80 moles) was added over 3 hours while maintaining the temperature at 75-80° C. After the addition was complete, the mixture was held for 1 hour at 75-80° C. The temperature was adjusted to 60° C. and water (121 g) charged. A 50% potassium hydroxide solution (182 g, 1.625 moles) added, followed by potassium iodide solution (1.5 g, 0.009 moles in water (3.5 g)). The pH was adjusted to pH 6.5 using 20% potassium bicarbonate (768 g of 20% solution). Additional water (81 g) was added and, after settling, the aqueous phase was separated from the organic phase.

The chlorobenzene was removed in vacuo and the remaining melt (300 g at 81% strength, 72.5% yield) distilled at 145-155° C. and 9 mbar to give the final product (222 g at 95.5% strength, 1.43 moles, 61.5% yield).

The invention claimed is:

1. A process for the preparation of 3-isochromanone which comprises the steps of:
   a) partially chlorinating o-tolylacetic acid with sulphuryl chloride or chlorine gas in an inert organic solvent in the presence of a free radical initiator to form a reaction mixture containing 2-chloromethylphenylacetic acid and unreacted o-tolylacetic acid;
   b) (i) treating the reaction mixture from step (a) with an aqueous salt-forming base to convert the 2-chloromethylphenylacetuic acid to 3-isochromanone and to form a salt of the unreacted o-tolylacetic acid; or
      (ii) extracting the 2-chloromethylphenylacetic acid and o-tolylacetic acid from the reaction mixture from step (a) at high pH with a strong aqueous base to give an aqueous solution of an o-tolylacetic acid salt and a 2-hydroxylmethylphenylacetic acid salt, acidifying the aqueous extract to convert the 2-hydroxymethylphenylacetic acid salt to 3-isochromanone and the o-tolylacetic acid salt to o-tolylacetic acid, and, in the presence of an added water-immiscible organic solvent, adjusting the pH with a salt-forming base to reconvert the o-tolylacetic acid to an o-tolylacetic acid salt;
   c) separating the 3-isochromanone from the salt of o-tolylacetic acid obtained in step (b) by a phase separation technique, the 3-isochromanone being dissolved in a water-immiscible organic solvent and the o-tolylacetic acid salt being dissolved in an aqueous solution; and
   d) converting the separated o-tolylacetic acid salt to o-tolylacetic acid by controlled acidification of the aqueous solution separated in step (c) to a pH of 4 or below, extracting the o-tolylacetic acid so formed into a solvent suitable for use in step (a) and recycling the solvent extract in a subsequent operation of step (a).

2. A process according to claim 1 in which the inert organic solvent is a water-immiscible solvent.

3. A process according to claim 1 in which the partial chlorination reaction is carried out at a temperature in the range of from 20° C. to 95° C.

4. A process according to claim 1 in which the o-tolylacetic acid is partially chlorinated by using from 0.2 to 1.2 moles of chlorinating agent for each mole of o-tolylacetic acid.

5. A process according claim 1 in which the free radical initiator is 2,2'-azobis (2-methylbutyronitrile) or 2,2'-azobisisobutyronitrile.

6. A process according to claim 1 in which, in step (b) (i) the reaction mixture from step (a) is treated with an aqueous salt-forming base to form directly 3-isochromanone and an o-tolylacetic acid salt at a controlled pH.

7. A process according to claim 6 in which the pH is controlled in the range of from 4 to 8.

8. A process according to claim 1 in which, in step (b)(ii) the high pH is a pH of 12 or more and the o-tolylacetic acid is converted to a salt by adjusting the pH in a range of from 6 to 8.

9. A process according to claim 1 in which step (b)(i) is carried out in the presence of a catalytic amount of potassium iodide.

10. A process according to claim 1 in which the water immiscible organic solvent containing 3-isochromanone obtained from step (c) is separated from the 3-isochromanone and recycled in a subsequence operation of the process, leaving a melt of 3-isochromanone which may be further purified.

11. A process according to claim 1 in which, in step (d), the o-tolylacetic acid salt is extracted from the aqueous phase by acidification in the presence of a water-immiscible solvent suitable for use in step (a) of the process and the solvent, containing dissolved o-tolylacetic acid, separated from the aqueous phase and recycled directly in a subsequent step (a).

12. A process according to claim 1, wherein step b) is step b)(i).

13. A process according to claim 1 wherein step b) is step b)(ii).

* * * * *